(12) United States Patent
Hedrick et al.

(10) Patent No.: US 8,476,428 B2
(45) Date of Patent: *Jul. 2, 2013

(54) METHOD OF PREPARING CYCLIC CARBONATES, CYCLIC CARBAMATES, CYCLIC UREAS, CYCLIC THIOCARBONATES, CYCLIC THIOCARBAMATES, AND CYCLIC DITHIOCARBONATES

(75) Inventors: James Lupton Hedrick, Pleasanton, CA (US); Alshakim Nelson, Fremont, CA (US); Daniel Paul Sanders, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/451,225

(22) Filed: Apr. 19, 2012

(65) Prior Publication Data
US 2012/0202993 A1    Aug. 9, 2012

Related U.S. Application Data

(63) Continuation of application No. 12/434,766, filed on May 4, 2009, now Pat. No. 8,178,700.

(51) Int. Cl.
*C07D 319/06*   (2006.01)
*C07D 265/06*   (2006.01)

(52) U.S. Cl.
USPC ............... 544/97; 544/315; 549/228; 549/14; 549/21

(58) Field of Classification Search
USPC .......................... 544/97, 315; 549/228, 14, 21
See application file for complete search history.

(56) References Cited

U.S. PATENT DOCUMENTS

| | | | |
|---|---|---|---|
| 4,102,912 A | 7/1978 | Carr | |
| 4,644,053 A | 2/1987 | Brunelle et al. | |
| 5,424,473 A | 6/1995 | Galvan et al. | |
| 6,300,458 B1 | 10/2001 | Vandenberg | |
| 6,664,372 B1 | 12/2003 | Janda et al. | |
| 7,893,274 B2 * | 2/2011 | Fujita et al. | .......... 548/227 |
| 2007/0015932 A1 | 1/2007 | Fujita et al. | |
| 2007/0232751 A1 | 10/2007 | Ludewig et al. | |
| 2010/0280242 A1 | 11/2010 | Hedrick et al. | |

OTHER PUBLICATIONS

USPTO, Non-Final Office Action in U.S. Appl. No. 12/434,766 to Hedrick, et al., filing date May 4, 2009, mailed Aug. 29, 2011.
Efimov, et al., "Dipentafluorophenyl carbonate—a reagent for the synthesis of oligonucleotides and their conjugates," Nucleic Acids Res. 1993, 21, 5337.
Fujita, et al., "Phosgene-Free Synthesis of N-Carboxyanhydrides of alpha-Amino Acids Based on Bisarylcarbonates as Starting Compounds," J. Polym. Sci. A. Polym. Chem. 2007, 45, 5365-5369.
Han, et al., "Azatides: Solution and Liquid Phase Syntheses of a New Peptidomimetic," JACS, 1996, 2539-2544.
Han, et al., "Investigations of Azapeptides as Mimetics of Leu-Enkephalin," Bioorg. Med. Chem. 1998, 8, 117-120.
Hedrick, et al., USPTO Office Action, U.S. Appl. No. 12/434,766, Aug. 29, 2011.
Hedrick, et al., USPTO Office Action, U.S. Appl. No. 12/434,766, Dec. 11, 2011.

* cited by examiner

*Primary Examiner* — Kahsay T Habte
(74) *Attorney, Agent, or Firm* — Michael R. Roberts

(57) ABSTRACT

A method of preparing a cyclic monomer, comprising: forming a first mixture comprising a precursor compound, bis (pentafluorophenyl)carbonate, and a catalyst; wherein the precursor compound has a structure comprising a) two or more carbons, and b) two functional groups selected from the group consisting of primary amine, secondary amine, thiol group, hydroxyl group, and combinations thereof; and agitating the first mixture at a temperature effective to form a second mixture comprising the cyclic monomer, the cyclic monomer selected from the group consisting of a cyclic carbonate, a cyclic carbamate, a cyclic urea, a cyclic thiocarbonate, a cyclic thiocarbamate, and a cyclic dithiocarbonate.

25 Claims, No Drawings

METHOD OF PREPARING CYCLIC CARBONATES, CYCLIC CARBAMATES, CYCLIC UREAS, CYCLIC THIOCARBONATES, CYCLIC THIOCARBAMATES, AND CYCLIC DITHIOCARBONATES

CROSS REFERENCE TO RELATED APPLICATIONS

This application is a continuation of, and claims the benefit of, pending nonprovisional U.S. application Ser. No. 12/434,766 entitled "METHOD OF PREPARING CYCLIC CARBONATES, CYCLIC CARBAMATES, CYCLIC UREAS, CYCLIC THIOCARBONATES, CYCLIC THIOCARBAMATES, AND CYCLIC DITHIOCARBONATES" filed on May 4, 2009, herein incorporated by reference in its entirety.

BACKGROUND

The present disclosure is generally related to a method of preparing cyclic monomers for ring-opening polymerizations, in particular cyclic carbonates, cyclic carbamates, cyclic ureas, cyclic thiocarbonates, cyclic thiocarbamates, and cyclic dithiocarbonates.

Technological advances continue to present many complex environmental issues. As a consequence, pollution prevention and waste management constitute two significant challenges of the $21^{st}$ century. "Green" chemistry is a concept that is being embraced around the world to insure continued economic and environmental prosperity. The interest in the U.S. began with the passage of the Pollution Prevention Act of 1990, the first law focused on the source rather than the remediation of the pollutants, which prompted the U.S. Environmental Protection Agency (EPA) to establish its green chemistry program in 1991. Since then, modern synthetic methodologies are encouraged to preserve performance while minimizing toxicity, use renewable feedstocks, and use catalytic and/or recyclable reagents to minimize waste. Green chemistry is the design and development of chemical products/processes that reduce or eliminate the use of substances harmful to our health or environment. What makes green chemistry such a powerful concept is that it starts at the molecular level and ultimately generates environmentally benign materials or material processes.

Phosgene is produced on a 10,000 ton scale per year for the formation of isocyanates (for making polycarbamates), polycarbonates (e.g., bisphenol A polycarbonate), and the formation of acid chlorides. Although phosgene is widely used, it is expensive and toxic. Phosgene was used in World War I as a chemical weapon and has been involved in tragic industrial accidents. Phosgene can be detected at 0.4 ppm which is only four times the U.S. maximum exposure limit. Phosgene is water-sensitive (reacting to form corrosive hydrogen chloride gas) and is therefore hazardous to store, ship, and handle. Diphosgene (trichloromethyl chloroformate) and triphosgene (bis(trichloromethyl)carbonate) are alternatives to phosgene with higher boiling points. While these compounds can be used to perform similar reactions with fewer handling difficulties, they still possess toxicities similar to phosgene. Moreover, handling of phosgene and tri-phosgene is labor intensive, and reactions must be performed at −78° C. with exhaustive work ups. Reaction of an active-hydrogen compound such as an alcohol, amine, or thiol with one of these phosgene-based reagents produces hydrochloric acid. The highly acidic hydrochloric acid can decompose acid-sensitive moieties in the starting material. Steps must be taken to scavenge this corrosive gas. These concerns add substantial cost to compounds produced with this reagent.

Known alternatives to phosgene include activated carbonyl compounds such as p-nitrophenyl chloroformate, trichloromethyl chloroformate, carbonyl diimidazole, bis(o- or p-nitrophenyl)carbonate, and bis(2,4-nitrophenyl)carbonate. However, these reagents often suffer from unwanted side reactions, difficult work ups, or lower reactivity.

Thus, a need exists for phosgene substitutes that are environmentally less toxic, less costly, and more compatible with the general goals of "green" chemistry.

BRIEF SUMMARY

The current method addresses the need for a "green" phosgene substitute in the preparation of cyclic carbonates, cyclic carbamates, cyclic ureas, cyclic thiocarbonates, cyclic thiocarbamates, and cyclic dithiocarbonates.

In one embodiment, a method of preparing a cyclic monomer comprises forming a first mixture comprising a precursor compound, bis(pentafluorophenyl)carbonate, and a catalyst; wherein the precursor compound has a structure comprising a) two or more carbons, and b) two functional groups selected from the group consisting of primary amine, secondary amine, thiol group, hydroxyl group, and combinations thereof; and agitating the first mixture at a temperature effective to form a second mixture comprising the cyclic monomer, the cyclic monomer selected from the group consisting of a cyclic carbonate, a cyclic carbamate, a cyclic urea, a cyclic thiocarbonate, a cyclic thiocarbamate, and a cyclic dithiocarbonate.

In another embodiment, a method of preparing a cyclic monomer, comprising: forming a first mixture comprising a bis(pentafluorophenyl)carbonate, a catalyst, and a precursor compound of the general formula (I):

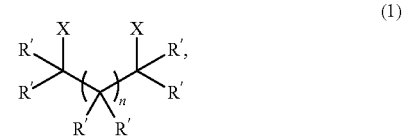

(1)

wherein each X group independently represents OH, NHR", $NH_2$, or SH; n is 0 to 6; each R' independently represents a hydrogen, a halide, an alkyl group comprising 1 to 20 carbons, an ester group comprising 1 to 20 carbons, an amide group comprising 1 to 20 carbons, an aryl group comprising 1 to 20 carbons, or an alkoxy group comprising 1 to 20 carbons; and each R" independently represents an alkyl group comprising 1 to 20 carbons or an aryl group comprising 1 to 20 carbons; and agitating the first mixture at a temperature effective to form a second mixture comprising the cyclic monomer, the cyclic monomer selected from the group consisting of a cyclic carbonate, a cyclic carbamate, a cyclic urea, a cyclic thiocarbonate, a cyclic thiocarbamate, and a cyclic dithiocarbonate.

In another embodiment, a method of preparing a cyclic monomer comprises forming a first mixture comprising bis (pentafluorophenyl)carbonate, a catalyst, and a precursor compound of the general formula (13):

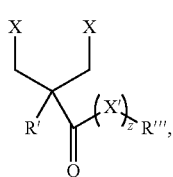

(13)

wherein X independently represents OH, NHR", NH$_2$, or SH; R' represents a hydrogen, a halide, an alkyl group comprising 1 to 20 carbons, an ester group comprising 1 to 20 carbons, an amide group comprising 1 to 20 carbons, an aryl group comprising 1 to 20 carbons, or an alkoxy group comprising 1 to 20 carbons; X' represents O, S, NH, or NR"; R" in X and X' independently represents an alkyl group comprising 1 to 20 carbons or an aryl group comprising 1 to 20 carbons; R'" represents an alkyl group comprising 1 to 20 carbons, or an aryl group comprising 1 to 20 carbons; and z is 0 or 1; and agitating the first mixture at a temperature effective to form a second mixture comprising the cyclic monomer, the cyclic monomer selected from the group consisting of a cyclic carbonate, a cyclic carbamate, a cyclic urea, a cyclic thiocarbonate, a cyclic thiocarbamate, and a cyclic dithiocarbonate.

Also disclosed is a biodegradable polymer derived from a cyclic monomer by ring-opening polymerization, the cyclic monomer derived from bis(pentafluorophenyl)carbonate.

Additional features and advantages are realized through the techniques of the present invention. Other embodiments and aspects of the invention are described in detail herein and are considered a part of the claimed invention. For a better understanding of the invention with the advantages and the features, refer to the description.

DETAILED DESCRIPTION

Disclosed is a method of preparing cyclic carbonates, cyclic carbamates, cyclic ureas, cyclic thiocarbonates, cyclic thiocarbamates, and cyclic dithiocarbonates using bis(pentafluorophenyl)carbonate (PFC), having the following structure:

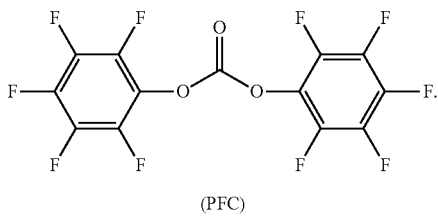

(PFC)

PFC is less toxic than phosgene. PFC is a crystalline solid at room temperature which, being less sensitive to water than phosgene, can be easily stored, shipped, and handled. PFC does not require elaborate reaction and workup conditions. Moreover, the pentafluorophenol byproduct produced during the disclosed cyclization reactions is less volatile, less acidic, and less corrosive than hydrochloric acid. These advantages reduce the cost and complexity of the reactions, and potentially widen the scope of the starting materials to include compounds containing acid-sensitive groups. In addition, the pentafluorophenol byproduct can be readily recycled back into PFC.

Bis(pentafluorophenyl)carbonate has been used previously in the bioorganic community as a coupling agent for oligonucleotides (see Efimov et al. *Nucleic Acids Res.* 1993, 21, 5337), for producing peptide mimics such as diazatides by Janda at Scripps (see: *Bioorg. Med. Chem.* 1998, 8, 117-120; JACS, 1996, 118, 2539-2544; and U.S. Pat. No. 6,664,372), and in the synthesis of N-carboxyanhydrides of amino acids (see: Fujita et al. *J. Polym. Sci. A. Polym. Chem.* 2007, 45, 5365-5369; and US Patent Publication 2007/0015932). However, bis(pentafluorophenyl)carbonate has not been used for the preparation of cyclic carbonates, cyclic carbamates, cyclic ureas, cyclic thiocarbonates, cyclic thiocarbamates, and cyclic dithiocarbonates.

The method comprises forming a first mixture containing a cyclic monomer precursor (referred to hereinafter as precursor compound) capable of forming a cyclic carbonate, cyclic carbamate, cyclic urea, cyclic thiocarbonate, cyclic thiocarbamate, or cyclic dithiocarbonate when reacted with PFC. The precursor compound has the general formula (I):

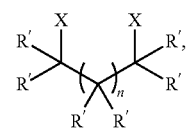

(1)

where each X independently represents OH, NHR", NH$_2$, or SH; n is 0 to 6, and R' independently represents a hydrogen, a halide, an alkyl group comprising 1 to 20 carbons, an ester group comprising 1 to 20 carbons, an amide group comprising 1 to 20 carbons, an aryl group comprising 1 to 20 carbons, or an alkoxy group comprising 1 to 20 carbons; and each R" independently represents an alkyl group comprising 1 to 20 carbons or an aryl group comprising 1 to 20 carbons. The R' and R" groups can independently comprise a cycloaliphatic ring, an aromatic ring, or a heteroatom such as oxygen, sulfur or nitrogen. When n is 0, the carbons attached to each X group are linked together by a single bond.

Thus, the precursor compound comprises at least the two carbons and two X groups. More particularly, the precursor compound has a functional group selected from 1,2-ethanediol group, 1,3-propanediol group, 1,4-butanediol group, 1,2-ethanediamine group, 1,3-propanediamine group, 1,4-butanediamine group, 2-aminoethanol group, 3-amino-1-propanol group, 4-amino-1-butanol group, 2-mercaptoethanol group, 3-mercapto-1-propanol group, 1-mercapto-2-propanol group, 4-mercapto-1-butanol group, cysteamine group, 1,2-ethanedithiol group, 1,3-propanedithiol group, or combinations thereof. In one embodiment, the PFC does not react with any R' group.

The precursor compounds can also include isomerically pure forms of the compounds and racemic mixtures. The isomerically pure compounds can have an enantiomeric excess of at least 90%, more specifically at least 95%, and even more specifically at least 98%.

Scheme 1 illustrates reactions using PFC and a catalyst to produce various cyclic monomers: trimethylene carbonate (3) from 1,3-propanediol (2); trimethylene urea (5) from 1,3-propanediamine (4), trimethylene carbamate (7) from 3-amino-1-propanol (6), trimethylene thiocarbonate (9) from 3-mercapto-1-propanol (8); and trimethylene dithiocarbonate (11) from 1,3-propanedithiol.

Scheme 1.

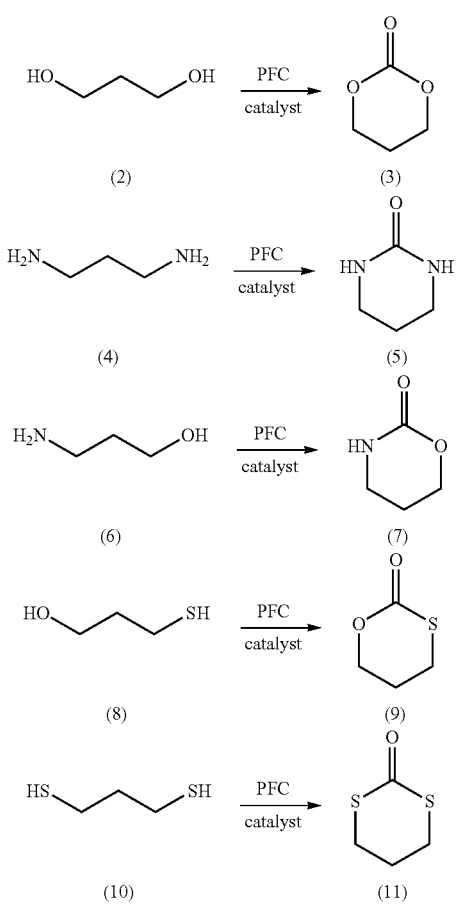

While a cyclic monomer such as (3) can be organocatalytically polymerized to form biocompatible and degradable materials, prior syntheses of (3) have required the use of toxic reagents such as phosgene or triphosgene. The procedures also involved workups requiring substantial time and energy that diminished the overall "greenness" of the process. PFC overcomes these issues and vastly improves the cost, safety, and environmental impact of producing cyclic monomers.

Cyclic monomers produced by the disclosed method are represented by the general formula (12):

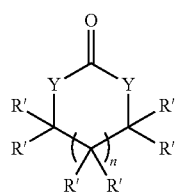

(12)

where each Y independently represents O, S, NH or NR"; each R' independently represents a hydrogen, a halide, an alkyl group comprising 1 to 20 carbons, an ester group comprising 1 to 20 carbons, an amide groups comprising 1 to 20 carbons, an aryl group comprising 1 to 20 carbons, or an alkoxy group comprising 1 to 20 carbons; each R" independently represents an alkyl group comprising 1 to 20 carbons or an aryl group comprising 1 to 20 carbons; and n is 0 to 6.

When n is 0, the methylene carbons bonded to each Y group are linked together by a single bond.

Exemplary substituted precursor compounds, where at least one R' group in formula (I) is a substituent other than hydrogen, include the materials of general formula (13):

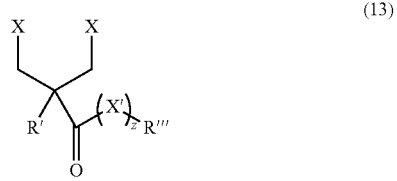

(13)

where X and R' have the meaning described above for formula (I); X' represents O, S, NH, or NR" where R" has the meaning described above for formula (I); R'" represents an alkyl group comprising 1 to 20 carbons, or an aryl group comprising 1 to 20 carbons; and z is 0 or 1. In one embodiment, each X in formula (13) is OH, X' is O, R' is a methyl or ethyl group, z is 1, and R'" is selected from the group consisting of methyl, ethyl, propyl, isopropyl, n-butyl, t-butyl, sec-butyl, n-pentyl, neo-pentyl, iso-pentyl, phenyl, pentafluorophenyl, xylyl, para-methoxyphenyl, benzyl, pentafluorobenzyl, n-octyl, and naphthyl.

The corresponding cyclic monomer formed by the precursor compounds of formula (13) have the general structure (14):

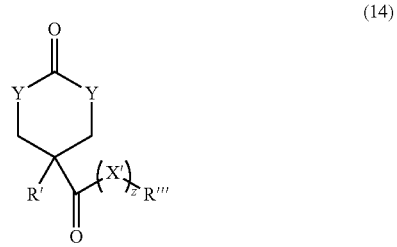

(14)

where Y, R', X', R'" and z have the same meaning described above.

Another challenge in preparing cyclic monomers, such as cyclic carbonates from 1,3-diols, is achieving selective ring closure without polymerization, which depends on the nucleophilicity of the leaving group and the catalyst used. During reaction of the precursor compound, PFC and catalyst, a pentafluorophenol byproduct is formed. The pentafluorophenol byproduct is a weak nucleophile and does not initiate polymerization. By comparison, when PFC is substituted with dimethyl carbonate, methanol is produced as the leaving group. Methanol is a stronger nucleophile than pentafluorophenol and causes significant amounts of undesirable polymer to be formed rather than the cyclic carbonate. In another example, when PFC is substituted with diimidazole carbonate, imidazole is released. Imidazole facilitates ring-closure and concurrent polymerization by activating the alcohol as an initiator. Thus, PFC is preferred over dimethyl carbonate or diimidazole carbonate since it produces less undesirable polymer byproduct. In an embodiment, the disclosed method produces 0 to less than 0.5 wt % polymer byproduct derived from the precursor compound, based on the weight of precursor compound. In another embodiment, the disclosed method produces no detectable polymer byproduct derived from the precursor compound.

The first mixture also includes a catalyst suitably chosen to activate the nucleophilic diol, amino-alcohol, diamine, mercapto-alcohol, amino-thiol, or dithiol functional groups and not the electrophilic PFC carbonyl group. Exemplary catalysts include tertiary amines, for example 1,8-bis(dimethylamino)naphthalene, referred to also as PROTON SPONGE, a trademark of Sigma-Aldrich. Other catalysts include halide salts of Group I elements, particularly lithium (Li), sodium (Na), potassium (K), rubidium (Rb), cesium (Cs), or francium (Fr). In one embodiment the catalyst is CsF.

The catalyst can be present in an amount of 0.02 to 1.00 moles per mole of the precursor compound, more particularly 0.05 to 0.50 moles per mole of the precursor compound, and even more particularly 0.15 to 0.25 moles per mole of the precursor compound.

The first mixture can optionally include a solvent such as tetrahydrofuran, methylene chloride, chloroform, acetone, methyl ethyl ketone, acetonitrile, ethyl acetate, butyl acetate, benzene, toluene, xylene, hexane, petroleum ethers, 1,4-dioxane, diethyl ether, ethylene glycol dimethyl ether, or combinations thereof. When a solvent is present, the concentration of precursor compound in the solvent can be 0.02 to 0.8 moles per liter, more specifically 0.1 to 0.6 moles per liter, or most specifically 0.15 to 0.25 moles per liter. In one embodiment, the reaction mixture consists of the precursor compound, PFC, a catalyst and a solvent. In one embodiment the solvent is anhydrous.

The method includes agitating the first mixture at a temperature suitable for converting the precursor compound to the cyclic monomer. The temperature can be from −20° C. to 100° C., 0° C. to 80° C., 10° C. to 50° C., or more specifically ambient or room temperature, typically 17° C. to 30° C. Optionally, the reaction mixture is agitated under an inert atmosphere. In one embodiment, the temperature is ambient temperature. The first mixture can be heated by conventional techniques involving resistive elements, or by microwaves. Microwaves can substantially reduce reaction times.

Agitation of the first mixture can be conducted for 1 hour to 120 hours, 5 hours to 48 hours, and more specifically 12 hours to 36 hours. In one embodiment, agitation is conducted for 15 to 24 hours at ambient temperature.

Agitation results in a second mixture comprising the cyclic monomer and the pentafluorophenol byproduct. The cyclic monomer can be isolated using any known method of purification, including distillation, chromatography, extraction, and precipitation. In one embodiment, the cyclic monomer is purified by selective precipitation of the pentafluorophenol byproduct or the cyclic monomer from the second mixture. In one variation on selective precipitation, the reaction mixture comprises a first solvent in which the precursor compound, PFC, cyclic monomer and pentafluorophenol byproduct are highly soluble. Upon completion of the reaction to form the cyclic monomer, the first solvent is removed by, for example, vacuum distillation, followed by addition of a second solvent suitably chosen to selectively precipitate the pentafluorophenol byproduct or the cyclic monomer. In another variation, the first solvent can be selected to facilitate precipitation of the cyclic monomer or the pentafluorophenol byproduct from the second mixture as the reaction proceeds.

The method can further comprise the step of recovering the pentafluorophenol byproduct for recycling. Because the disclosed cyclization reactions do not consume pentafluorophenol, two moles of pentafluorophenol are produced for every mole of PFC used. Generally, the yield of recovered pentafluorophenol byproduct from the second mixture is about 100 to 200 mole percent, more particularly 150 to 200 mole percent, and even more particularly 180 to 200 mole percent based on moles of PFC used in the first mixture. In an embodiment, the pentafluorophenol is quantitatively recovered from the second mixture.

Also disclosed are the cyclic monomers produced by the above-described method, wherein the cyclic monomer is derived from bis(pentafluorophenyl)carbonate and a precursor compound selected from the group consisting of diol, amino-alcohol, diamine, mercapto-alcohol, amino-thiol, and dithiol, and combinations thereof. More specifically, the cyclic monomer can be a cyclic carbonate selected from the group consisting of dimethylene carbonate, propylene carbonate, trimethylene carbonate, tetramethylene carbonate, pentamethylene carbonate, and MTC-Bn. Further, the cyclic monomer can be a cyclic carbamate selected from the group consisting of dimethylene carbamate, propylene carbamate, trimethylene carbamate (TMU), tetramethylene carbamate, and pentamethylene carbamate. Still further, the cyclic monomer can be a cyclic urea selected from the group consisting of dimethylene urea, trimethylene urea, tetramethylene urea, and pentamethylene urea. Yet another cyclic monomer can be a cyclic thiocarbonate selected from the group consisting of dimethylene thiocarbonate, propylene thiocarbonate, trimethylene thiocarbonate, tetramethylene thiocarbonate. Still another cyclic monomer can be a cyclic thiocarbamate selected from the group consisting of dimethylene thiocarbamate, propylene thiocarbamate, trimethylene thiocarbamate, tetramethylene thiocarbmate. Finally, the cyclic monomer can be a cyclic dithiocarbonate selected from the group consisting of dimethylene thiocarbonate, propylene thiocarbonate, trimethylene thiocarbonate, tetramethylene thiocarbonate.

The cyclic monomers include isomerically pure forms of the cyclic monomers and racemic mixtures.

The cyclic monomers can undergo ring-opening polymerization (ROP) to form biodegradable polymers of different tacticities. Atactic, syndiotactic and isotactic forms of the polymers can be produced that depend on the cyclic monomer(s), its isomeric purity, and the polymerization conditions.

A method of ring-opening polymerization comprises forming a first mixture comprising the cyclic monomer, a catalyst, an initiator, and an optional solvent. The first mixture is then heated and agitated to effect polymerization of the cyclic monomer, forming a second mixture containing the biodegradable polymer product.

The ring opening polymerization is generally conducted in a reactor under inert atmosphere such as nitrogen or argon. The polymerization can be performed by solution polymerization in an inactive solvent such as benzene, toluene, xylene, cyclohexane, n-hexane, dioxane, chloroform and dichloroethane, or by bulk polymerization. The ROP reaction temperature can be from about room temperature to 250° C. Generally, the reaction mixture is heated at atmospheric pressure for 0.5 to 72 hours to effect polymerization. Subsequently, additional cyclic monomer and catalyst can be added to the second mixture to effect block polymerization if desired.

Exemplary catalysts for the ROP polymerization include metal oxides such as tetramethoxy zirconium, tetra-iso-propoxy zirconium, tetra-iso-butoxy zirconium, tetra-n-butoxy zirconium, tetra-t-butoxy zirconium, triethoxy aluminum, tri-n-propoxy aluminum, tri-iso-propoxy aluminum, tri-n-butoxy aluminum, tri-iso-butoxy aluminum, tri-sec-butoxy aluminum, mono-sec-butoxy-di-iso-propoxy aluminum, ethyl acetoacetate aluminum diisopropylate, aluminum tris(ethyl acetoacetate), tetraethoxy titanium, tetra-iso-propoxy titanium, tetra-n-propoxy titanium, tetra-n-butoxy titanium, tetra-sec-butoxy titanium, tetra-t-butoxy titanium, tri-iso-propoxy gallium, tri-iso-propoxy antimony, tri-iso-butoxy antimony, trimethoxy boron, triethoxy boron, tri-iso-propoxy boron, tri-n-propoxy boron, tri-iso-butoxy boron, tri-n-butoxy boron, tri-sec-butoxy boron, tri-t-butoxy boron, tri-iso-propoxy gallium, tetramethoxy germanium, tetraethoxy germanium, tetra-iso-propoxy germanium, tetra-n-propoxy germanium, tetra-iso-butoxy germanium, tetra-n-butoxy germanium, tetra-sec-butoxy germanium and tetra-t-butoxy germanium; halogenated compound such as antimony pentachloride, zinc chloride, lithium bromide, tin(IV) chloride, cadmium chloride and boron trifluoride diethyl ether; alkyl aluminum such as trimethyl aluminum, triethyl aluminum, diethyl aluminum chloride, ethyl aluminum dichloride and tri-iso-butyl aluminum; alkyl zinc such as dimethyl zinc, diethyl zinc and diisopropyl zinc; tertiary amines such as triallylamine, triethylamine, tri-n-octylamine and benzyldimethylamine; heteropolyacids such as phosphotungstic acid, phosphomolybdic acid, silicotungstic acid and alkali metal salt thereof; zirconium compounds such as zirconium acid chloride, zirconium octanoate, zirconium stearate and zirconium nitrate. More particularly, the catalyst is zirconium octanoate, tetraalkoxy zirconium or a trialkoxy aluminum compound.

Other ROP catalysts include metal-free organocatalysts that can provide a platform to polymers having controlled, predictable molecular weights and narrow polydispersities. Examples of organocatalysts for the ROP of cyclic esters, carbonates and siloxanes are 4-dimethylaminopyridine, phosphines, N-heterocyclic carbenes (NHC), bifunctional aminothioureas, phosphazenes, amidines, and guanidines.

The ROP reaction mixture comprises at least one catalyst and, when appropriate, several catalysts together. The ROP catalyst is added in a proportion of $1/20$ to $1/40,000$ moles relative to the cyclic monomers, and preferably of $1/1,000$ to $1/20,000$ moles.

The ROP reaction mixture also comprises an initiator. Initiators generally include nucleophiles such as alcohols, amines and thiols. The initiator can be monofunctional, difunctional or multifunctional such as dendritic, polymeric or related architectures. Monofunctional initiators can include nucleophiles with protected functional groups that include thiols, amines, acids and alcohols. A typical initiator is phenol or benzyl alcohol.

Well-known apparatuses can be used for performing the ROP polymerization. An example of a tower type reaction apparatus ise a reaction vessel comprising helical ribbon wings and transformational spiral baffles. An example of sideways type reaction apparatus is a sideways type one- or twin-shaft kneader comprising agitation shafts which have a row of transformational wings and arranged in parallel to each other. In addition, the reaction apparatus may be either a batch type or a continuous one.

The biodegradable ROP product can be in the form of a homopolymer, copolymer, or block copolymer. The biodegradable polymer can have a number-average molecular weight of usually 1,000 to 200,000, more particularly 2,000 to 100,000, and still more particularly 5,000 to 80,000.

The biodegradable polymer product of the ROP polymerization can be applied to conventional molding methods such as extrusion molding, injection molding, hollow molding and vacuum molding, and can be converted to molded articles such as various parts, receptacles, materials, tools, films, sheets and fibers. A molding composition can be prepared comprising the biodegradable polymer and various additives, including for example nucleating agents, pigments, dyes, heat-resisting agents, antioxidants, weather-resisting agents, lubricants, antistatic agents, stabilizers, fillers, strengthened materials, fire retardants, plasticizers, and other polymers. Generally, the molding compositions comprise 30 wt. % to 100 wt. % or more of the biodegradable polymer based on total weight of the molding composition. More particularly, the molding composition comprises 50 wt. % to 100 wt. % of the biodegradable polymer.

The following examples illustrate the method of preparing a cyclic monomer.

EXAMPLES

Examples 1-3

Preparation of Methyl-5-Benzyloxycarboxyl-1,3-Dioxan-2-One (MTC-Bn)—Optimization of Solvent

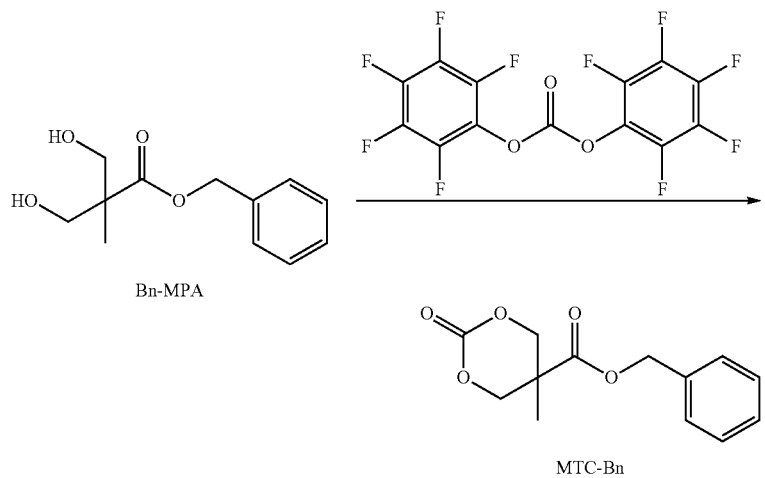

Example 1

In a flask, benzyl 2,2-bis(methylol)propionate (Bn-MPA) (0.500 g, 0.00222 mol, 1 eq.) was placed in tetrahydrofuran (THF, 20 ml), followed by PFC (0.875 g, 0.00222 mol, 1 eq.). CsF (84 mg, 0.555 mmol, 0.25 eq.) was added as a solid, and the solution was stirred for 24 hours at room temperature. A small aliquot was dried, and the solvent was replaced with CDCl$_3$. Proton NMR of the crude product indicated approximately 70% conversion to 5-methyl-5-benzyloxycarboxyl-1,3-dioxan-2-one (MTC-Bn), and no trace of polycarbonate.

Example 2

In a flask, Bn-MPA (0.500 g, 0.00222 mol, 1 eq.) was placed in dichloromethane (DCM, 15 ml), followed by PFC (0.875 g, 0.00222 mol, 1 eq.). CsF (84 mg CsF, 0.555 mmol, 0.25 eq.) was added as a solid, and the solution was stirred for 24 hours at room temperature. A small aliquot was dried out, and the solvent was replaced by CDCl$_3$. Proton NMR of the crude indicated approximately 50% conversion to MTC-Bn, and no trace of polycarbonate.

Example 3

In a flask, Bn-MPA (0.500 g, 0.00222 mol, 1 eq.) was placed in acetone (20 ml), followed by PFC (0.875 g, 0.00222 mol, 1 eq.). CsF (84 mg, 0.555 mmol, 0.25 eq.) was added as a solid, and the solution was stirred for 24 hours at room temperature. A small aliquot was dried, and the solvent was replaced by CDCl$_3$. Proton NMR of the crude indicated approximately 90% conversion to MTC-Bn, and no trace of polycarbonate.

Examples 4-5

Preparation of MTC-Bn—Optimization of Stoichiometry

Example 4

In a flask, Bn-MPA (0.250 g, 0.00111 mol, 1 eq.) was placed in THF (15 ml), followed by PFC (0.660 g, 0.00333 mol, 1.5 eq.). CsF (42 mg, 0.277 mmol, 0.25 eq.) was added as a solid, and the solution was stirred for 24 hours at room temperature. A small aliquot was dried, and the solvent was replaced by CDCl$_3$. Proton NMR of the crude indicated approximately 95% conversion to MTC-Bn, and no trace of polycarbonate.

Example 5

In a flask, Bn-MPA (0.250 g, 0.00111 mol, 1 eq.) was placed in THF (15 ml), followed by PFC (0.660 g, 0.00166 mol, 1.5 eq.). CsF (42 mg, 0.277 mmol, 0.25 eq.) was added as a solid, and the solution was stirred for 24 hours at room temperature. A small aliquot was dried out, and solvent was replaced by CDCl$_3$. Proton NMR of the crude indicates approximately 95% conversion to MTC-Bn, and more importantly no trace of polycarbonate.

Examples 6

Preparation of MTC-Bn with PROTON SPONGE

Example 6

In a flask, Bn-MPA (0.500 g, 0.00222 mol, 1 eq.) was placed in THF, followed by PFC (0.875 g, 0.00222 mol, 1 eq.). Then PROTON SPONGE (119 mg, 0.555 mmol, 0.25 eq.) was added, and solution was stirred for 24 hours at room temperature. A small aliquot was dried, and the solvent was replaced by CDCl$_3$. Proton NMR of the crude indicates approximately 70% conversion to MTC-Bn, and no trace of polycarbonate. The solution color was pink/orange.

Example 7

Preparation of MTC-Bn with CsF

Example 7

In a 20 mL glass vial, Bn-MPA (500 mg, 2.25 mmol), bis(pentafluorophenyl)carbonate (1.32 g, 3.35 mmol), cesium fluoride (67 mg, 0.44 mmol, 0.20 eq), and dry THF (5 mL) were added and stirred for 16 hours at room temperature. After the solvent was evaporated from the inhomogeneous mixture methylene chloride (15 mL) was added to the residue, and the insoluble material was filtered. The filtrate was then washed with saturated aqueous NaHCO$_3$ (2×20 mL), dried over MgSO$_4$, filtered and evaporated to give MTC-Bn as a white solid (402 mg, 71.6%).

Example 8

Synthesis of Trimethyleneurethane (TMU)

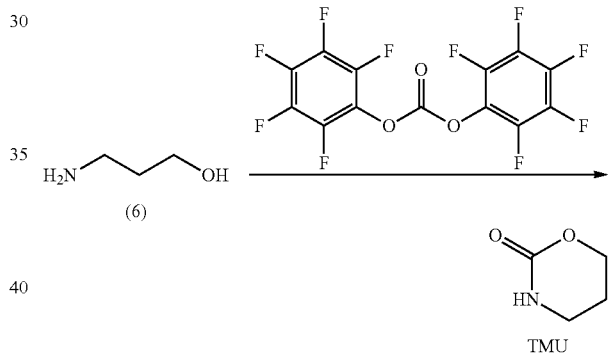

Example 8

3-Amino-1-propanol, (6), (2.29 mL, 30.0 mmol) was dissolved in THF (40 mL) in a 100 mL round-bottom flask and the solution was cooled to −5° C. with ice-salt bath. A solution of PFC (13.02 g, 33.1 mmol) in dry THF (25 mL) was added stepwise over 30 min, at which point the reaction mixture was allowed to warm to room temperature for 2 hours. CsF (0.91 g, 6.0 mmol, 0.20 eq) was added to the mixture prior to overnight stirring. The solvent was removed in vacuo, and the resulting residue was dissolved in methylene chloride, cooled and filtered to remove insoluble material. The filtrate was dried under vacuum to yield a pale amber solid as a crude product, which was recrystallized in a mixture of ethyl acetate and hexane. The crystalline compound was then heated to about 100° C. under vacuum until no signal was observed in $^{19}$F NMR. The molten residue was cooled to room temperature to provide the isolated product, TMU, as a white solid (1.86 g, 61.2%). $^1$H NMR (400 MHz, CDCl$_3$): δ 5.87 (b, 1H, NH), 4.30 (t, 2H, CH$_2$O), 3.38-3.36 (m, 2H, CH$_2$N), 2.02-1.96 (m, 2H, CH$_2$). $^{13}$C NMR (100 MHz, DMSO-d$_6$): δ 152.7, 66.1, 38.8, 20.9.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention.

While preferred embodiments to the invention have been described, it will be understood that those skilled in the art, both now and in the future, may make various changes that fall within the scope of the claims which follow. These claims should be construed to maintain the proper protection for the invention described.

What is claimed is:

1. A method of preparing a cyclic monomer, comprising:
   forming a first mixture comprising a precursor compound, bis(pentafluorophenyl) carbonate, and a catalyst; wherein the precursor compound has a structure comprising a) two or more carbons, and b) two functional groups independently selected from the group consisting of primary amine, secondary amine, thiol group, hydroxyl group, and combinations thereof; and
   agitating the first mixture at a temperature effective to form a second mixture comprising the cyclic monomer, the cyclic monomer selected from the group consisting of a cyclic carbonate, a cyclic carbamate, a cyclic urea, a cyclic thiocarbonate, a cyclic thiocarbamate, and a cyclic dithiocarbonate.

2. The method of claim 1 wherein the first mixture comprises a solvent.

3. The method of claim 1, wherein the catalyst is a tertiary amine.

4. The method of claim 1, wherein the catalyst is 1,8-bis(dimethylamino)naphthalene.

5. The method of claim 1, wherein the catalyst is a halide salt of at least one of the following: lithium, sodium, potassium, rubidium, and cesium.

6. The method of claim 1, wherein the reaction mixture comprises from 0 to less than 0.5 wt % of a polymer byproduct derived from the precursor compound, based on a weight of precursor compound.

7. The method of claim 1, wherein the precursor compound has an asymmetric center, and the precursor compound has an isomeric purity characterized by an enantiomeric excess of 80% to 100%.

8. The method of claim 1, wherein agitating the reaction mixture at ambient temperature forms a pentafluorophenol byproduct, and the method further comprises recovering the pentafluorophenol byproduct.

9. The method of claim 1, wherein the cyclic carbonate is selected from the group consisting of dimethylene carbonate, propylene carbonate, trimethylene carbonate, tetramethylene carbonate, and pentamethylene carbonate.

10. The method of claim 1, wherein the cyclic carbamate is selected from the group consisting of dimethylene carbamate, propylene carbamate, trimethylene carbamate (TMU), tetramethylene carbamate, and pentamethylene carbamate.

11. The method of claim 1, wherein the cyclic urea monomer is selected from the group consisting of dimethylene urea, trimethylene urea, tetramethylene urea, and pentamethylene urea.

12. The method of claim 1, wherein the cyclic thiocarbonate monomer is selected from the group consisting of dimethylene thiocarbonate, propylene thiocarbonate, trimethylene thiocarbonate, and tetramethylene thiocarbonate.

13. The method of claim 1, wherein the cyclic thiocarbamate monomer is selected from the group consisting of dimethylene thiocarbamate, propylene thiocarbamate, trimethylene thiocarbamate, and tetramethylene thiocarbamate.

14. The method of claim 1, wherein the cyclic dithiocarbonate monomer is selected from the group consisting of dimethylene dithiocarbonate, propylene dithiocarbonate, trimethylene dithiocarbonate, tetramethylene dithiocarbonate.

15. The method of claim 1, wherein each of the two functional groups is a hydroxyl group, and the cyclic monomer is a cyclic carbonate.

16. The method of claim 1, wherein one of the two functional groups is a hydroxyl group, another of the two functional groups is a primary amine, and the cyclic monomer is a cyclic carbamate.

17. The method of claim 1, wherein one of the two functional groups is a hydroxyl group, another of the two functional groups is a secondary amine, and the cyclic monomer is a cyclic carbamate.

18. The method of claim 1, wherein one of the two functional groups is a hydroxyl group, another of the two functional groups is a thiol, and the cyclic monomer is a cyclic thiocarbonate.

19. The method of claim 1, wherein each of the two functional groups is a primary amine, and the cyclic monomer is a cyclic urea.

20. The method of claim 1, wherein each of the two functional groups is a secondary amine, and the cyclic monomer is a cyclic urea.

21. The method of claim 1, wherein one of the two functional groups is a primary amine, another of the two functional groups is a secondary amine, and the cyclic monomer is a cyclic urea.

22. The method of claim 1, wherein one of the two functional groups is a primary amine, another of the two functional groups is a thiol, and the cyclic monomer is a cyclic thiocarbamate.

23. The method of claim 1, wherein one of the two functional groups is a secondary amine, another of the two functional groups is a thiol, and the cyclic monomer is a cyclic thiocarbamate.

24. The method of claim 1, wherein each of the two functional groups is a thiol, and the cyclic monomer is a cyclic dithiocarbonate.

25. The method of claim 5, wherein the catalyst is cesium fluoride (CsF).

* * * * *